(12) United States Patent
Jertz

(10) Patent No.: US 10,297,433 B2
(45) Date of Patent: May 21, 2019

(54) SUPPRESSING HARMONIC SIGNALS IN ION CYCLOTRON RESONANCE MASS SPECTROMETRY

(71) Applicant: Bruker Daltonik GmbH, Bremen (DE)

(72) Inventor: Roland Jertz, Bremen (DE)

(*) Notice: Subject to any disclaimer, the term of this patent is extended or adjusted under 35 U.S.C. 154(b) by 331 days.

(21) Appl. No.: 15/201,786

(22) Filed: Jul. 5, 2016

(65) Prior Publication Data

US 2018/0012741 A1 Jan. 11, 2018

(51) Int. Cl.
| | |
|---|---|
| *G01N 27/62* | (2006.01) |
| *H01J 49/00* | (2006.01) |
| *H01J 49/36* | (2006.01) |
| *H01J 49/38* | (2006.01) |

(52) U.S. Cl.
CPC .......... *H01J 49/0036* (2013.01); *H01J 49/38* (2013.01); *G01N 27/622* (2013.01); *H01J 49/0031* (2013.01); *H01J 49/36* (2013.01)

(58) Field of Classification Search
CPC .................................. H01J 49/00; H01J 49/38
See application file for complete search history.

(56) References Cited

U.S. PATENT DOCUMENTS

| | | | | |
|---|---|---|---|---|
| 8,766,174 B1* | 7/2014 | Baykut | ................... | H01J 49/38 |
| | | | | 250/282 |
| 8,859,953 B2 | 10/2014 | Baykut et al. | | |
| 9,304,106 B1* | 4/2016 | Park | ........................ | H01J 49/06 |
| 9,355,830 B2 | 5/2016 | Baykut et al. | | |
| 9,620,349 B2 | 4/2017 | Roeck et al. | | |
| 9,865,446 B2* | 1/2018 | Kovtoun | ................ | H01J 49/423 |
| 2004/0011953 A1* | 1/2004 | Chen | ...................... | H01J 49/067 |
| | | | | 250/288 |
| 2005/0178961 A1 | 8/2005 | Beu et al. | | |
| 2008/0270083 A1* | 10/2008 | Lange | ................ | G06K 9/00523 |
| | | | | 702/193 |
| 2009/0084948 A1* | 4/2009 | Baykut | .............. | G06Q 10/0633 |
| | | | | 250/282 |
| 2010/0176289 A1 | 7/2010 | Franzen | | |
| 2014/0224972 A1* | 8/2014 | Baykut | .................... | H01J 49/38 |
| | | | | 250/252.1 |

(Continued)

FOREIGN PATENT DOCUMENTS

DE 102014226498 A1 6/2016

*Primary Examiner* — Michael J Dalbo
(74) *Attorney, Agent, or Firm* — Benoît & Côté Inc.

(57) ABSTRACT

The invention relates to reducing harmonic signals in FT-ICR spectra. Since harmonic signals in quadrupolar 2ω-detection can be more abundant for the same ion motion in the ICR cell as compared to harmonic signals in classical dipolar 1ω-detection, they could hitherto not be reduced to satisfactory levels by any known method, such as gated deflection during ion introduction into, and correcting for an offset electric field axis in the ICR cell. The present disclosure foresees, in addition to other methods carried out for improving the measurement conditions as the case may be, performing the quadrupolar 2ω-detection at least twice, where the phase of the ion excitation radio frequency is turned by 180° in the second measurement. From the sum transient, a Fourier-transformed spectrum is derived. As a result, the broad band spectra of complex substance mixtures like crude oil become cleaner, and misinterpretations of false (harmonic) peaks are minimized.

20 Claims, 11 Drawing Sheets

(56) References Cited

U.S. PATENT DOCUMENTS

| | | | |
|---|---|---|---|
| 2015/0179420 A1* | 6/2015 | Senko | H01J 49/06 250/282 |
| 2016/0181080 A1* | 6/2016 | Williams | H01J 49/063 250/292 |
| 2016/0181083 A1* | 6/2016 | Roeck | H01J 49/022 250/282 |
| 2017/0032950 A1* | 2/2017 | Tsybin | H01J 49/0031 |

* cited by examiner

SUPPRESSING HARMONIC SIGNALS IN ION CYCLOTRON RESONANCE MASS SPECTROMETRY

BACKGROUND OF THE INVENTION

Field of the Invention

The invention relates to a method for the reduction and elimination of harmonic signals in ion cyclotron resonance frequency or mass spectra. These undesired harmonic signals may generate peaks, particularly in broad band spectra of complex mixtures of organic substances, which could be erroneously interpreted as true ionic peaks. In multiple electrode $n\omega$-detection where the $n\nu = n\omega/2\pi$ resonance frequency is measured as the fundamental frequency, high abundant subharmonic signals deteriorate the spectra and complicate their interpretation. Specifically, in quadrupolar $2\omega$-detection, $1\nu$-subharmonic signals can appear at undesired high abundance.

Description of the Related Art

Ion cyclotron resonance mass spectrometry (ICR-MS) can be conducted in a wide range of operation modes. With extreme narrow band operation, detecting only ion species in a mass (m/z) range around a single Dalton, extremely high mass resolutions on the order of several ten millions ($R = m/\Delta m > 10^7$) can be achieved from transients measured up to five minutes or more. Extremely good ultra-high vacuum ($p < 10^{-7}$ Pascal) is required to minimize the number of collisions between the orbiting ions and residual gas molecules in the cell. The ultra-high mass resolution enables analysis of the fine structure of isotope satellites of the molecular ion species. This reveals the elemental composition of the ion species, facilitating the determination of a total formula for analytes in the sample under investigation.

On the other hand, broad band operation covering mass ranges of some thousand Daltons offers qualitative and quantitative analysis of complex mixtures of hundreds of organic substances with somewhat reduced mass resolution of some millions ($R > 10^6$), and mass precisions of about one part per million (1 ppm). Since as many as hundreds or thousands of individual ion species may occupy the cyclotron orbit, the usable lengths of image current transients are typically reduced to a few seconds only. Examples for these complex mixture analyses are crude oils, oil distillation residues, or mixtures of natural substances extracted from plants when looking for pharmaceutically interesting ingredients or reagents, for instance.

In ICR cells, the axis of the magnetron motion should be theoretically identical with the ICR cell axis, but experience tells that quite often the axis of the ionic magnetron orbit in a cylindrical ICR cell shows a radial offset from the geometric axis of the cell. The offset magnetron orbit adversely influences the cyclotron excitation as well as the detection process of the ions. It also impairs the detected signal; in the classical dipolar $1\omega$-detection it leads to an increase of the intensity of the peaks associated with the even-numbered (e.g. second) harmonics in the Fourier transformed spectrum and further to more abundant sidebands of the ion signal. In extreme cases, ions can be lost during the cyclotron excitation, which typically comprises a pulse radio frequency sweep (so-called "chirp"), when they are on large or largely offset magnetron orbits that displace the ions critically close to the (cylinder) mantle electrodes.

If the ICR cell components in ICR-MS are somewhat misaligned, the spectra will become complex by the appearance of harmonic signals of larger peaks or by peaks representing sidebands from the superposition of cyclotron and magnetron oscillations. In narrow band ICR, these peaks do not play a prominent role because they are usually far away from the signals under investigation. But in broad band ICR mass spectrometry, it would be helpful to suppress these peaks as much as possible, because they tend to appear in ranges of interest of the frequency or mass spectrum, and can greatly complicate the interpretation of such spectrum.

A skilled practitioner will acknowledge that an asymmetry of the electric field inside the cell can be a consequence of many different reasons, e.g. a deviation of the individual electrode shapes from the ideal ones or a deviation of the complete assembled cell from its ideal shape, resulting in different kinds of harmonics. Symmetry errors of the electric field inside the ICR cell may also arise from asymmetric contact potentials of connectors from the power supply.

Asymmetric electric fields in the ICR cell can also be a consequence of charging-up of individual electrodes. Charging is a general process, which can appear due various reasons, one of which could be a high resistive connection of an electrode to ground. Normally, after every acquisition cycle, the detection electrodes in the cell should be at ground potential. However, if they are connected to ground over a large resistor, which enables the picking-up of induced image charge signals of very low amplitude, the swiftness and ease of the discharge after every acquisition cycle may be adversely affected. Consequently, the electrode may maintain its charged state for a while, even after the next acquisition cycle starts. As a result, an asymmetric electric field is induced in the cell due to an electrode being incompletely discharged. A different type of electrode charging is surface charging. This usually happens if the metallic surface of the electrode carries a dielectric layer, which can be polarized or charged and cannot easily be discharged due to its lack of conductance. Cleaning would be a viable countermeasure for such contamination.

Document U.S. Pat. No. 8,766,174 B1 (G. Baykut et al.) describes methods and devices for optimization of electric fields in measurement cells of Fourier transform ion cyclotron resonance mass spectrometers. This document shall be incorporated herein by reference in its entirety. The optimization is based on the rationale that offset and asymmetric electric fields can appear in ion cyclotron resonance cells and therefore the axis of the magnetron orbit can become radially displaced. Shifted magnetron orbits negatively affect the cyclotron excitation, deteriorate the FT-ICR signal, increase the intensity of the even-numbered harmonic signals (in dipolar $1\omega$-detection), lead to stronger side bands of the FT-ICR signal, and in extreme cases, cause loss of ions. The method helps in probing the shift of the magnetron motion, detecting parameters indicative of the offset of the electric field axis and correcting it by trimming it back to the geometric axis of the ICR cell. This results in a decrease or complete elimination of even-numbered harmonic peaks, which is most clearly observed by the decrease of the harmonic peak $2\nu_+$. A further document (U.S. Pat. No. 9,355,830 B2; G. Baykut et al.), also incorporated herein by reference in its entirety, describes how to minimize the magnetron orbit radius by gated deflection during the introduction of ions into the ICR cell. Hereby, the sideband peaks of the FT-ICR signal and its harmonic peaks are reduced. In dipolar $1\omega$-detection the effect is most clearly observed for the most abundant sideband peak ($2\nu_+ + \nu_-$). But, both methods can also be applied to multiple electrode $n\omega$-detection.

As stated above, for complex mixtures of substances it is broad band operation that is called for, but the short transients reduce the mass resolution significantly. To improve broad band mass resolution in spite of the shortness of the measureable transients, a multiple electrode measurement of the cyclotron frequencies may be applied; e.g. a quadrupolar $2\omega$-detection results in a measurement of the double frequency $2v_+$. These $2\omega$-measurements generate mass spectra with double the mass resolution as compared with dipolar $1\omega$-measurements, but unfortunately also usually produce subharmonic signals with the frequency $1v$ of all genuine mass peaks. A good trimming and tuning according to documents U.S. Pat. No. 8,766,174 B1 and U.S. Pat. No. 9,355,830 B2 can help to reduce the subharmonic peaks $1v_+$ and their sideband harmonic peak s $(v_++v_-)$ to about 1 percent of the measured fundamental $2v_+$ peak; but there is still a need to further reduce the $1v$-subharmonic signals, such as by about another factor of ten, in order to obtain yet increased evaluability of the acquired transients. The intensity of the subharmonic peaks $(v_++v_-)$ is space charge dependent; it might not be stable after trimming in different applications, or makes the trimming very difficult due to low intensity signals

SUMMARY OF THE INVENTION

In view of the foregoing, the invention pertains in a first aspect to a method for reducing $1v$-subharmonic signals in measurements of ICR mass spectra by quadrupolar $2\omega$-detection of transients representing the ionic image currents in an ICR cell after excitation of ions. The method comprises the steps of (dipolar) exciting a first bunch of ions using a first (start) phase of the excitation wave and measuring a first transient by quadrupolar $2\omega$-detection, (dipolar) exciting a second bunch of ions using a second excitation wave (start) phase differing from the first phase by about 180°, and measuring a second transient by quadrupolar $2\omega$-detection, adding the first and second transients, and transforming the sum of the first and second transients into a frequency spectrum (or a mass spectrum or m/z spectrum).

The first aspect of the invention relates to the $2\omega$-detection of the cyclotron frequency with a quadrupolar arrangement of detection electrodes and dipolar arrangement of the excitation electrodes. The invention proposes to perform this quadrupolar $2\omega$-measurement two times with two bunches of ions (having substantially the same ionic composition), wherein the phase of the excitation wave is turned by substantially 180° for the second measurement, and the two transients are added together. As a result, the $1v$-subharmonic signals are greatly reduced in the frequency and mass spectra which are obtained by suitable transformations of the sum of the transients.

The method is favorably applied to a broad band measurement spanning an m/z range of equal to or more than 1000 Dalton up to several thousands of Daltons.

In various embodiments, the first and second bunches of ions are preferably derived from a complex substance mixture, such as crude oil, oil distillation residue, or a plant extract.

The first and the second bunches of ions might advantageously comprise substantially equal numbers of ions. To achieve this, the ions of the first and second bunches of ions can be generated in an ion source which operates at substantially constant ionic output, and may be transferred to the ICR cell using a same transfer procedure (including various ion funnels, ion guides and/or ion traps as the case may be).

In various embodiments, the ion source can be fed with substances from a substance separator, such as a (liquid) chromatograph or an electrophoretic device. When doing so, the first and second transients are preferably measured immediately subsequently in order to guarantee substantially the same ionic composition in the different ion bunches.

In an alternative of the method, a first sum-transient may be obtained by adding measured transients from several bunches of ions using excitation at the first phase, and a second sum-transient is obtained in a similar way but using excitation at the second phase, and the first and second sum-transients can be added to obtain the frequency spectrum by Fourier transforming the overall sum spectrum. In a further modification, the first and second sum-transients could be obtained by alternately measuring (at correspondingly alternating excitation wave phases) and adding transients from several bunches of ions.

In various embodiments, also a phase of the detection can be switched by about 180° between the measurement of the first and second transients, and the $1v$-harmonic signals found therein might be used to precisely determine the unperturbed cyclotron frequency $v_c$. If both excitation phase and detection phase are turned by 180° in subsequent transient acquisitions, the signal of the measured fundamental frequency $2v_+$ disappears, and the signal of the subharmonic peak $1v_+$ and its side band peak $(v_++v_-)$ remains enhanced. This alternative method can be used to precisely determine mass values by measuring the side band frequency $(v_++v_-)$ which is in fact the unperturbed cyclotron frequency $v_c$ in the ICR cell. This frequency is independent of the electrical (axial) trapping potential of the ICR cell; hence magnetron movement and space charge perturbations will not influence the measurements, which can result in higher accuracy of the mass determination.

In various embodiments, the ICR cell may comprise four quarter cylindrical mantle electrodes and two axial trapping electrodes, and the excitation can include irradiating the ICR cell with a pulse radio frequency sweep ("chirp"), as is well known to one of skill in the art.

In a second aspect, the invention pertains to a method for measuring ion cyclotron resonance transients that represent the ionic image currents in an ICR cell, having multiple 2×n mantle electrodes where n>2 is an integer, after excitation of ions. The method comprises the steps of (dipolar) exciting a first bunch of ions using a first excitation wave phase and measuring a first transient by multiple electrode $n\omega$-detection, (dipolar) exciting a second bunch of ions using a second excitation wave phase differing from the first phase by about 180°, and measuring a second transient by multiple electrode $n\omega$-detection, and adding the first and second transients to form a sum transient, which may be transformed into a frequency or mass (m/z) spectrum.

The second aspect applies the principles of the invention to multi electrode $n\omega$-detection with n>2. So doing will reduce the $(n-1, n-3, n-5, \ldots)v$-subharmonic signals and the higher frequency $(n+1, n+3, n+5, \ldots)v$-harmonic signals and their sidebands. But very high abundant signals of the $(n-2, n-4, n-6, \ldots)v$-subharmonic signals and higher frequency $(n+2, n+4, n+6, \ldots)v$-harmonic signals and their sidebands might still appear. In the case of $3\omega$-detection, the scheme of excitation wave phase switching can be different in that the excitation wave phase is switched by 180° together with the detection phase for subsequent transient acquisitions.

DETAILED DESCRIPTION

While the invention has been shown and described with reference to a number of different embodiments thereof, it will be recognized by those of skill in the art that various changes in form and detail may be made herein without departing from the scope of the invention as defined by the appended claims.

In a first aspect, the invention aims to suppress the 1v-subharmonic signals in broad band spectra obtained by quadrupolar 2ω-detection. In spectra of complex mixtures of substances, these signals complicate the interpretation. In broad band spectra measurement, the measurable transients are usually short, only a few seconds, reducing the achievable mass resolution. To enhance the resolution by a factor of two, quadrupolar 2ω-detection can be applied, but the 1v-subharmonics disturb the spectra.

Figure 1:
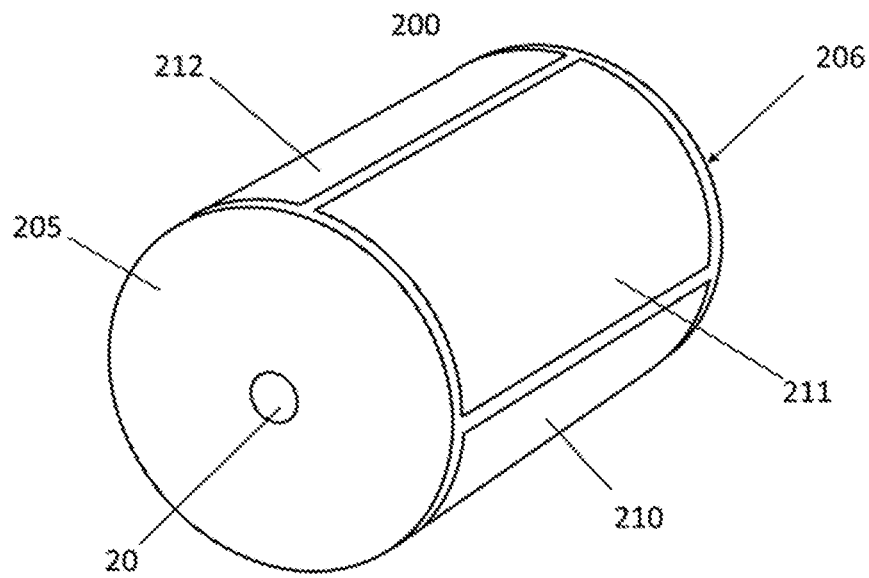
FIG. 1 shows a simple form of a cylindrical ICR cell (200) with four cylinder mantle electrodes (210) to (212) and two end cap (axial trapping) electrodes (205) and (206).
Figure 2:
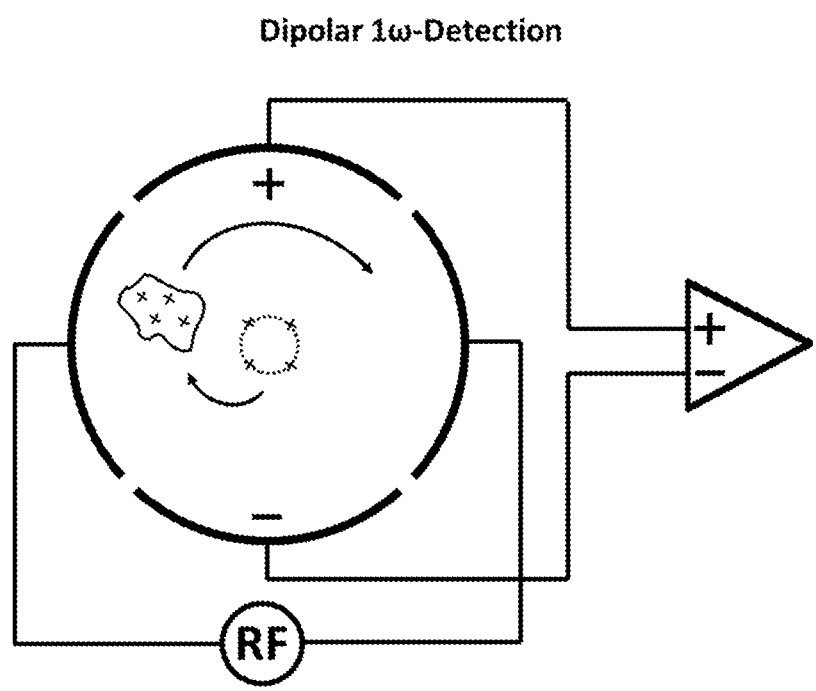
FIG. 2 exhibits a schematic diagram of the classical operation of an FT-ICR cell using dipolar excitation and dipolar 1ω-detection.
Figure 3A:
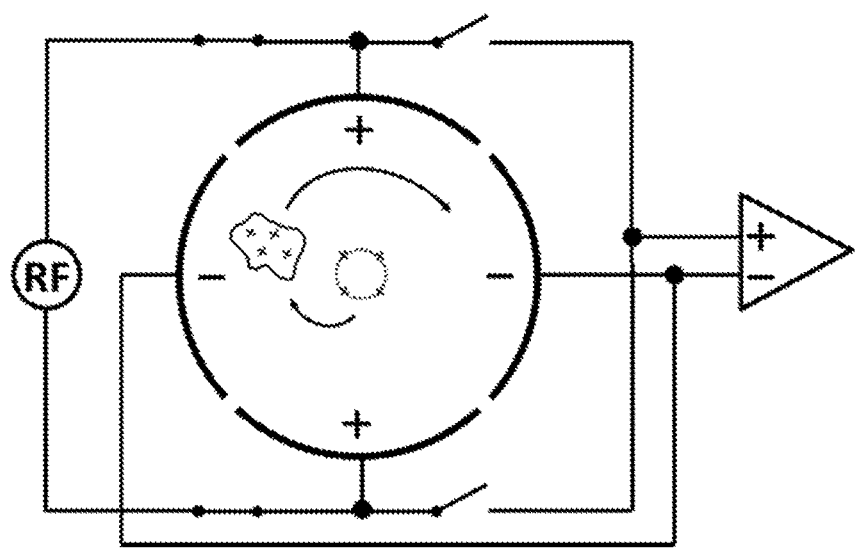
FIG. 3a schematically presents the circuit status of the dipolar excitation for a quadrupolar 2ω-detection measurement.
Figure 3B:
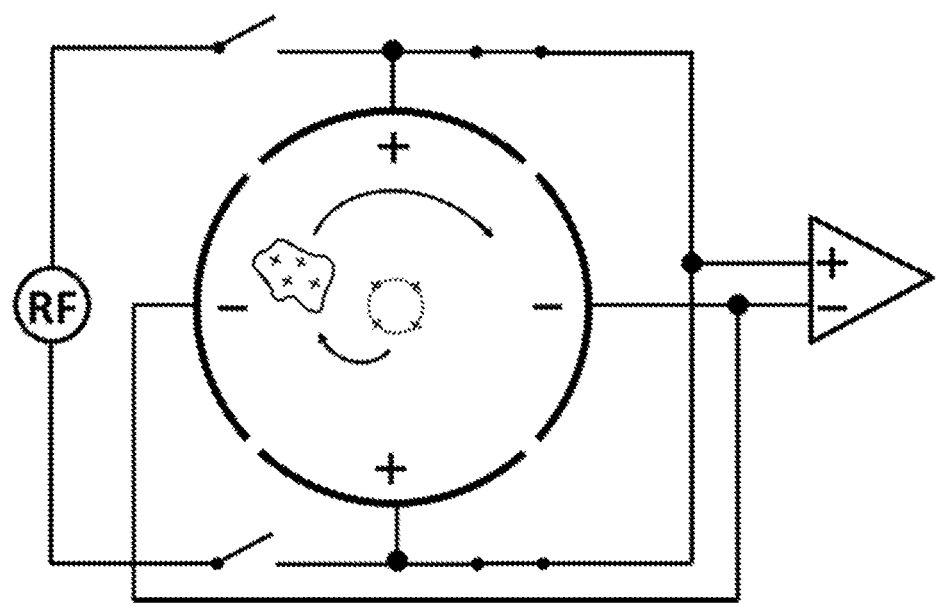
FIG. 3b shows the quadrupolar 2ω-detection.

The first aspect relates to the 2ω-measurement of the cyclotron frequency, such as conducted with a quadrupolar arrangement of quarter cylindrical excitation and detection electrodes, as shown by way of example in FIG. 1. The principle of quadrupolar 2ω-measurements is illustrated in FIG. 3a and FIG. 3b, exhibiting the switching states for the excitation and detection events. To suppress the 1v-subharmonics, this quadrupolar 2ω-measurement is performed two times, wherein the phase of the excitation wave is turned by 180° for the second measurement, and the two transients are added together. As a result, the signals of the 1v-subharmonics are greatly reduced or even eliminated beyond detectability.

Figure 4:
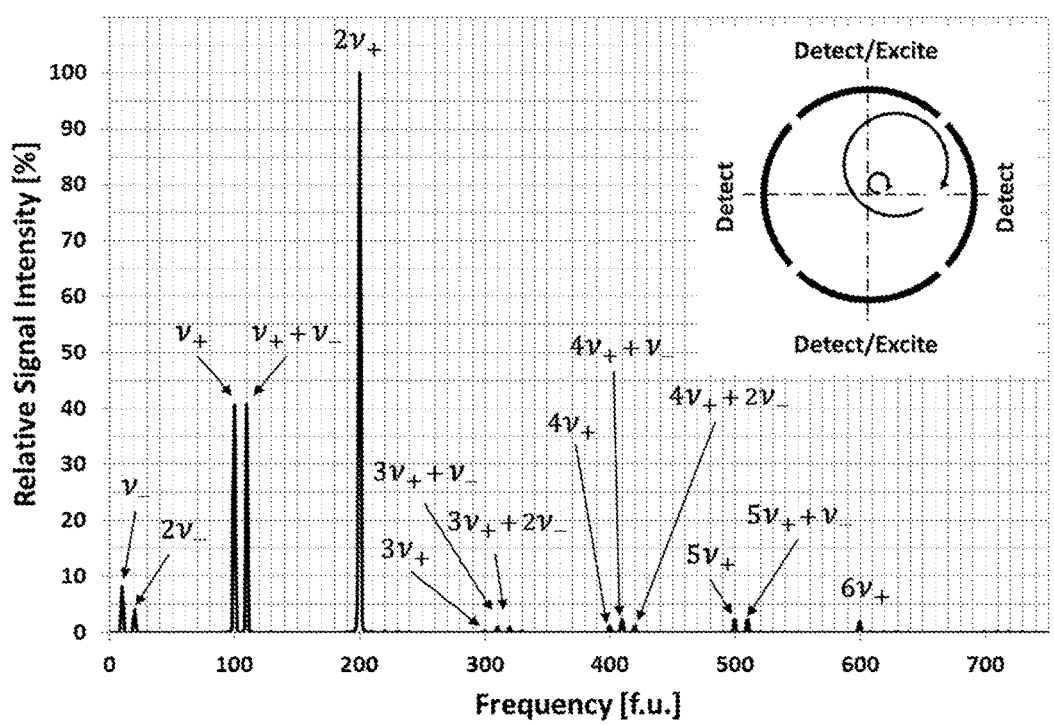
FIG. 4 shows, in some detail, a simulated frequency spectrum as obtained from a Fourier transformation of a transient simulating a quadrupolar 2ω-measurement, without using a subharmonic suppression method according to principles of this invention. The simulations were done with a cyclotron orbit of 50% of the ICR cell radius, 10% magnetron orbit, and 10% offset between magnetron center and axis of the ICR cell (illustrated in the insert at the top right). The main signal represents the fundamental peak $2v_+$; next in size is the group of the 1v-subharmonics, comprising the cyclotron frequency $v_+$ and its side band $(v_+ + v_-)$. Furthermore, third, fourth, fifth and sixth harmonics are visible towards larger frequencies as tiny peaks.

The result can be studied by computer simulations, an example of which is presented in FIG. 4. Here, the cyclotron orbit radius is assumed to amount to 50% of the ICR cell radius, and the magnetron orbit radius to 10% of the ICR cell radius. The center of the magnetron orbit has an offset of about 10% from the axis of the ICR cell. The orbit positions of cyclotron and magnetron are illustrated in the insert at the top right. Under these conditions, a frequency spectrum will be obtained as exhibited in FIG. 4. The designation $v_+$ represents the cyclotron frequency, $v_-$ represents the magnetron frequency. As expected, the most abundant peak appears at $2v_+$, the double cyclotron frequency; but surprisingly the 1v-subharmonics group ($v_+$; $v_+ + v_-$) has an intensity of about 40% of the main peak. The higher frequency harmonics groups (3v, 4v, 5v and 6v) are visible but have largely negligible intensities.

Figure 5:
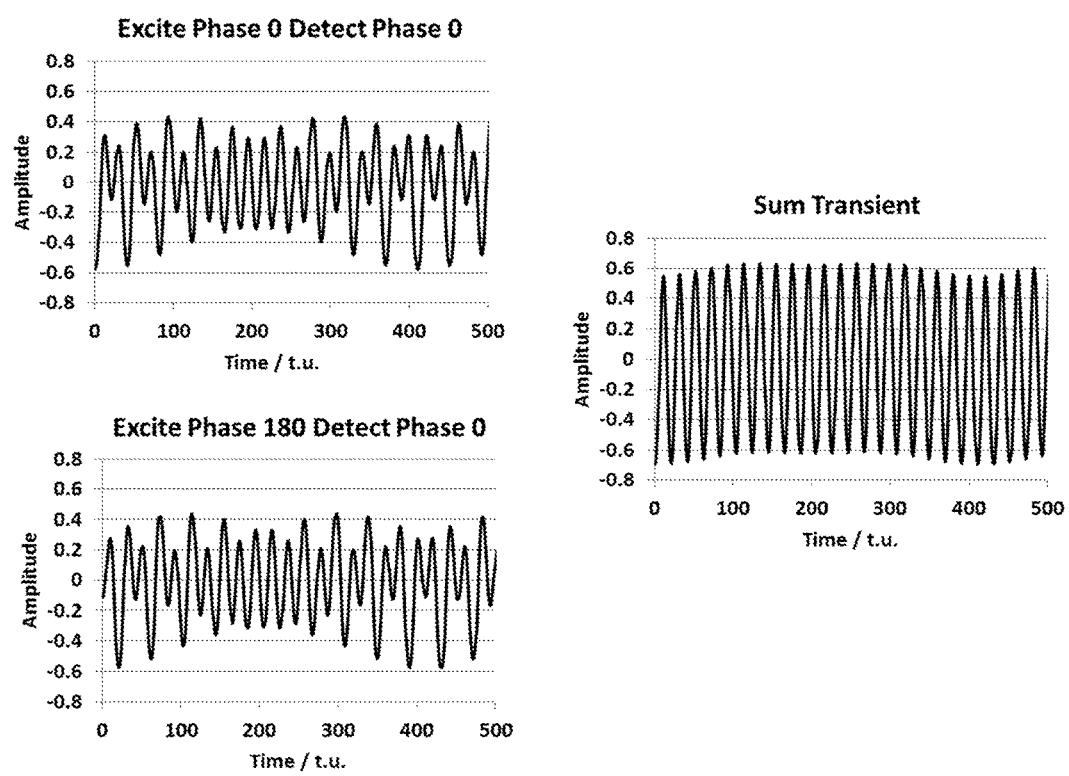
FIG. 5 shows on the left-hand side two excerpts of simulated transients as measured by quadrupolar 2ω-detection, wherein the measurement at the bottom was obtained with an excitation wave phase turned by 180° compared with the excitation wave phase used for the transient at the top. The addition of both transients is shown on the right-hand side.
Figure 6A:
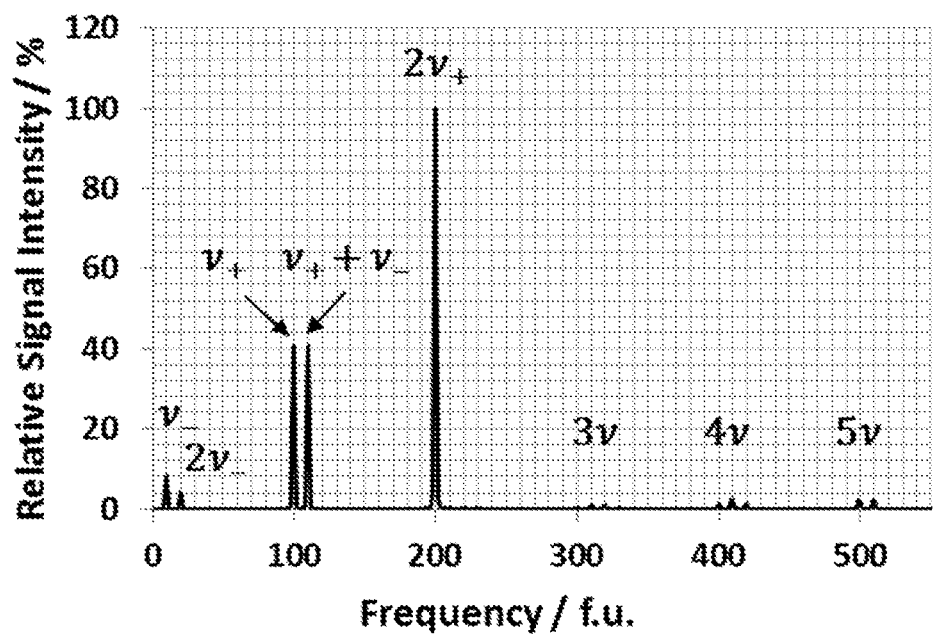
FIG. 6a presents the frequency spectrum, which is identical for each of the two transients shown on the left-hand side of FIG. 5.
Figure 6B:
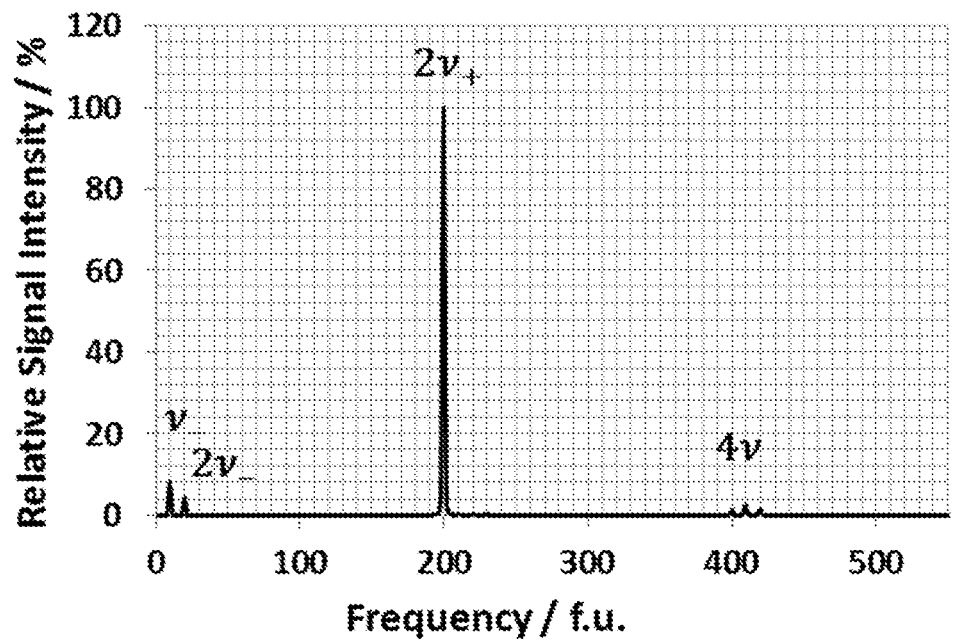
FIG. 6b shows the frequency spectrum of the summed transient on the right-hand side of FIG. 5. The group of 1v-subharmonic signals completely disappears (and also the groups of third and fifth harmonic signals).

FIGS. 5, 6a, and 6b show the simulation result of the suppression according to principles of this invention. FIG. 5 depicts on the left-hand side two excerpts of simulated transients as measured by 2ω quadrupolar detection, wherein the measurement at the bottom was obtained with an excitation phase turned by 180° compared with the excitation phase used for the transient at the top. The addition of both transients, the basic idea of this invention, is shown on the right-hand side of the figure. FIG. 6b now presents the frequency spectrum of the summed transient on the right-hand side of FIG. 5. As intended by the invention, the 1v-subharmonics group ($v_+$; $v_+ + v_-$) completely disappears, and also the groups of higher frequency third and fifth harmonics. In contrast, FIG. 6a presents the frequency spectrum of one of the left-hand side transients of FIG. 5 showing the original spectrum with all subharmonics and higher frequency harmonics.

Figure 7:
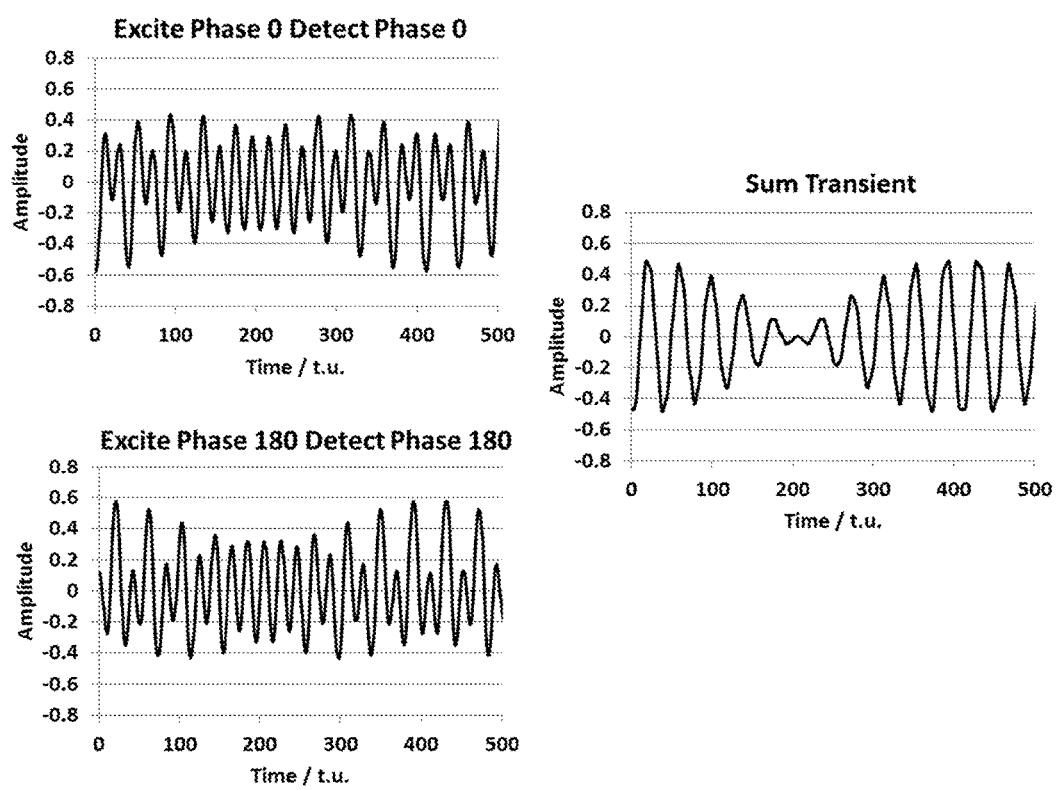
FIG. 7 again shows on the left-hand side two excerpts of simulated transients as measured by quadrupolar 2ω-detection, wherein the measurement at the bottom was obtained with both excitation and detection phases turned by 180° compared with the phases of the first measured transient at the top. The addition of both transients is shown on the right-hand side, now showing a kind of beat.
Figure 8A:
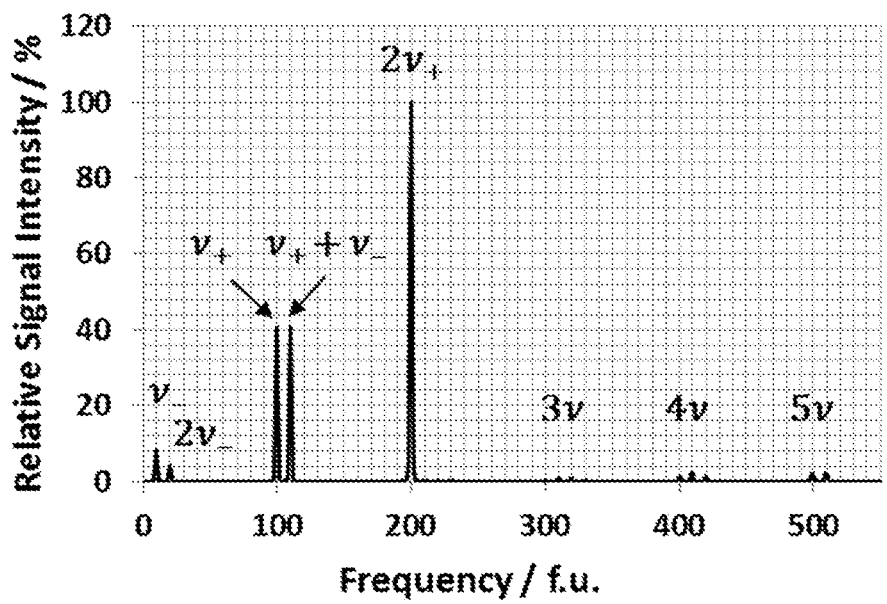
FIG. 8a presents the frequency spectrum, which is identical for each of the two transients shown on the left-hand side of FIG. 7.
Figure 8B:
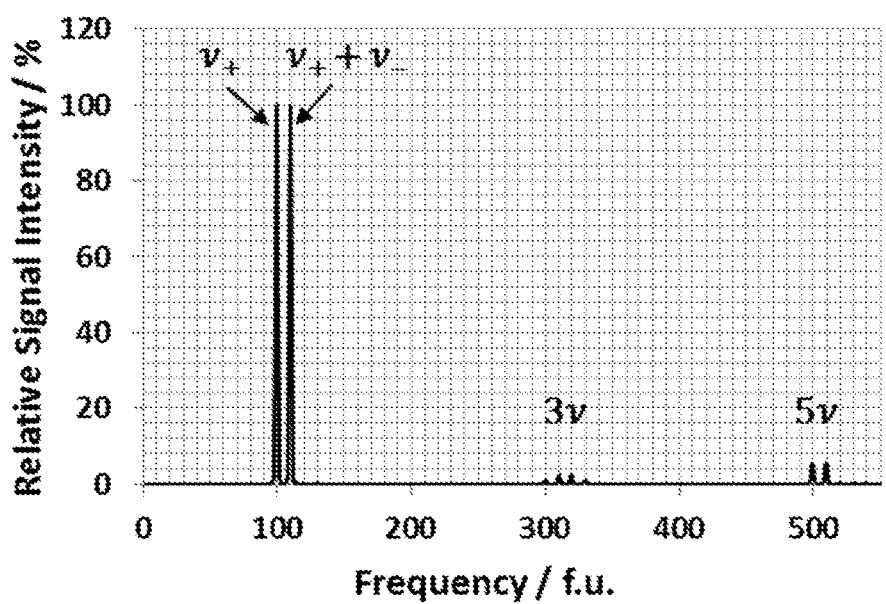
FIG. 8b shows the frequency spectrum of the summed transient on the right-hand side of FIG. 7. Now, the fundamental cyclotron peak $2v_+$ disappears (and also the group of fourth harmonic signals), while the group of 1v-subharmonics takes full size. This method can be used to precisely measure the side band frequency $(v_+ + v_-)$ which is in fact the unperturbed cyclotron frequency $v_c$ in the ICR cell. This frequency is not influenced by the electrical (axial) trapping potential of the ICR cell, i.e. by magnetron movement and space charge perturbations.

If both excitation wave phase and detection phase are turned by 180°, the $2v_+$ signal, i.e. the double fundamental frequency, disappears, and the signal of the 1v-subharmonics group ($v_+$; $v_+ + v_-$) remains, as demonstrated by FIGS. 7, 8a, and 8b. This method can be used to precisely determine frequency or mass values by measuring the side band frequency ($v_+ + v_-$) which is in fact the unperturbed cyclotron frequency $v_c$ in the ICR cell. This frequency is not influenced by the electrical (axial) trapping potential of the ICR cell, i.e. by magnetron movement and space charge perturbations.

Figure 9:
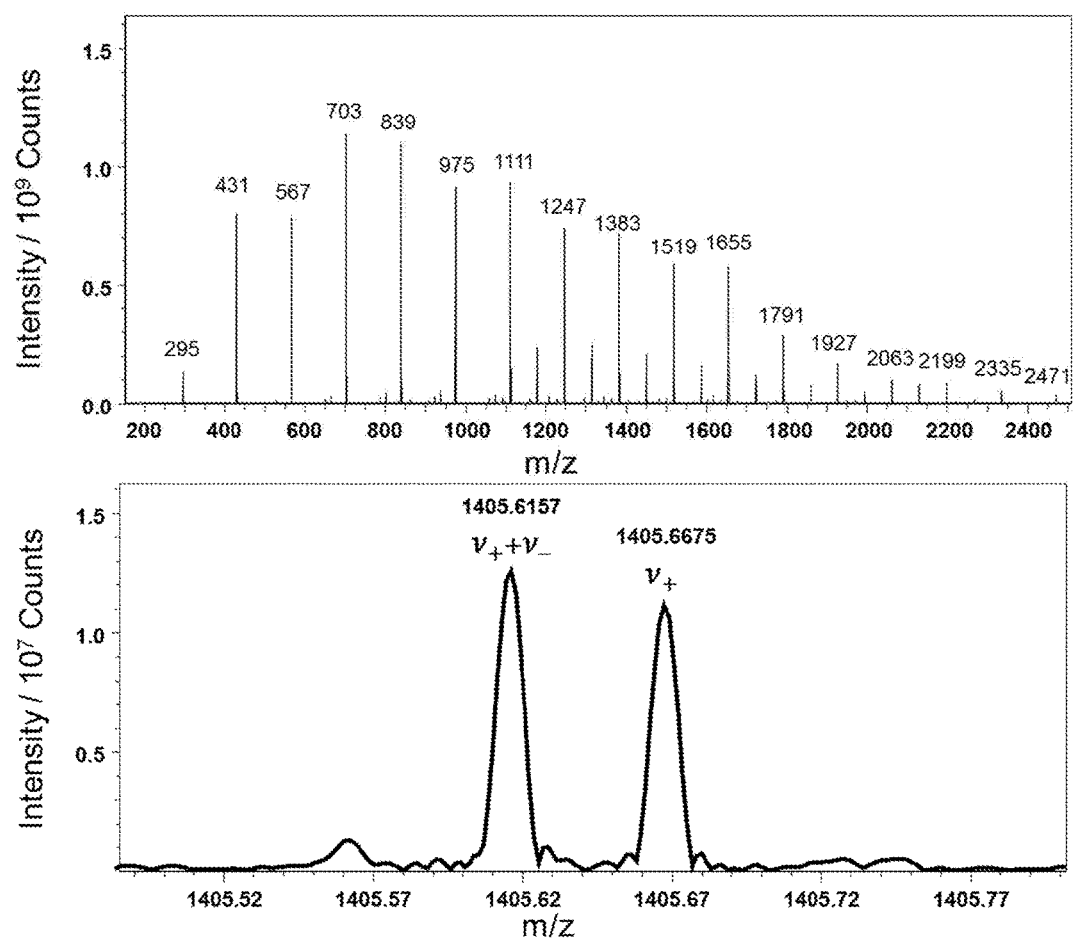
FIG. 9 exhibits in the upper panel a measured (not simulated) broadband FT-ICR mass spectrum of sodium trifluoroacetate (NaTFA) that mainly consists of a series of cluster ion peaks, with the strongest peak at m/z 703 Dalton. In the lower panel, FIG. 9 displays a closer view of the group of first subharmonics of this strongest peak, appearing at m/z 1405.6 Dalton, magnified in intensity by a factor of 100, and zoomed-in on the m/z scale. The intensity of this group of peaks, not representing true ionic signals in the spectrum, amounts to about 1 percent of its fundamental peak, potentially giving rise to some misinterpretation of the spectrum. Similar harmonic peaks may be visible for all other mass peaks of the spectrum.
Figure 10:
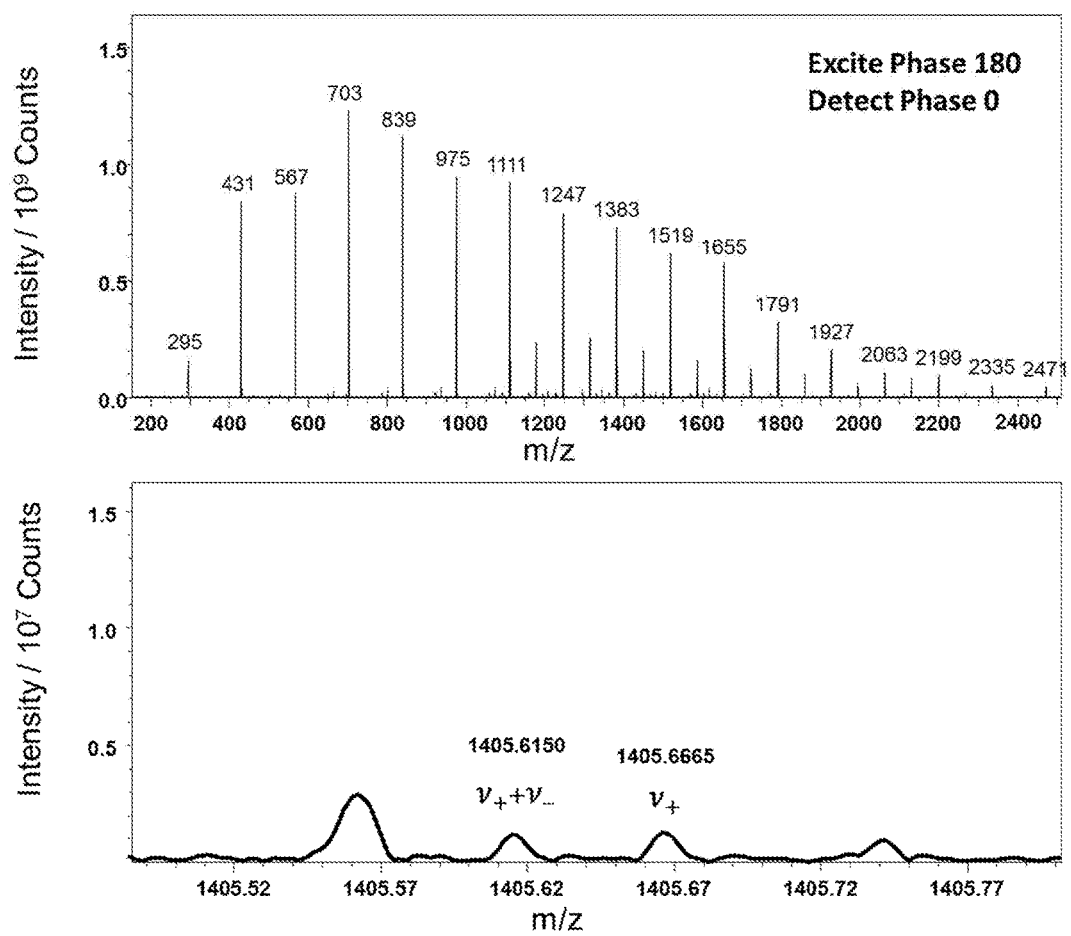
FIG. 10 demonstrates the effect of the method according to principles of the invention. The intensities of the first harmonics of the spectrum peaks now are reduced by a factor of about ten.

Real measurements of the effect of the invention are presented in FIG. 9 and FIG. 10. In both figures, the upper panel shows measured mass spectra of sodium trifluoroacetate (NaTFA), which forms numerous cluster ions. In the bottom panels of the figures, the 1v-subharmonics group of the main mass peak of 703 Dalton is shown, appearing around m/z 1405.6, enlarged in intensity by a factor of 100, and zoomed-in on the mass scale. In FIG. 9, after application of the shimming and gated deflection methods described in U.S. Pat. No. 8,766,174 B1 and U.S. Pat. No. 9,355,830 B2, respectively, but without application of the method presented herein, the intensities of the 1v-subharmonics amount to about 1% of the corresponding fundamental $2v_+$ peak. In FIG. 10, applying in addition the principles according to the invention, the signals of the 1v-subharmonics ($v_+$; $v_+ + v_-$) are reduced in size by a factor of about ten.

Figure 11:
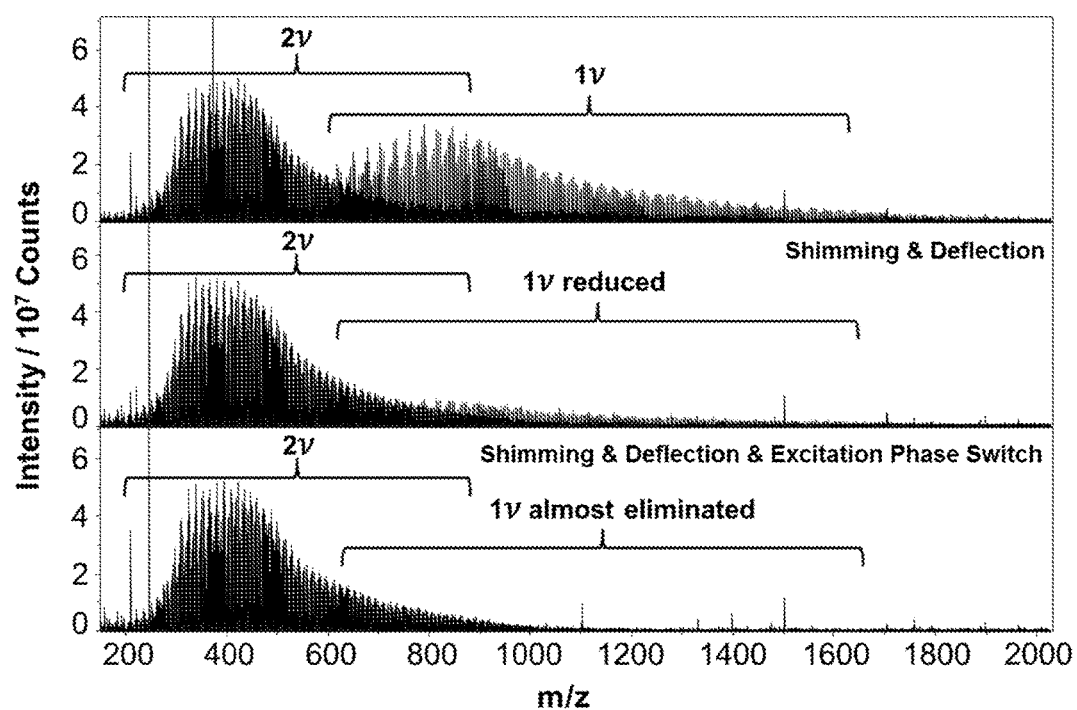
FIG. 11 shows three measurements of a complex mixture sample SRFA (Suwannee River Fulvic Acids). In the uppermost spectrum, the ICR cell was not correctly trimmed. In the middle spectrum, the cell was almost optimally trimmed and filled using the methods described in U.S. Pat. No. 8,766,174 B1 and U.S. Pat. No. 9,355,830 B2, respectively. The 1v-subharmonic signals were greatly reduced but did not completely disappear. In the mass spectrum at the bottom, the excitation phase switching according to principles of this invention was used additionally to almost completely eliminate the 1v-subharmonic signals.

FIG. 11 shows spectra of measurements of a complex mixture sample SRFA (Suwanee River Fulvic Acids) acquired with three different methods. In the uppermost spectrum, the ICR cell was not correctly trimmed by shimming and gated deflection. In the middle spectrum, the cell was optimally trimmed according to the methods described in the documents U.S. Pat. No. 8,766,174 B1 and U.S. Pat. No. 9,355,830 B2 for the optimization of electric fields and reduction of the magnetron orbit in measurement cells of Fourier transform ion cyclotron resonance mass spectrometers. The 1v-subharmonic signals are greatly reduced but do not completely disappear. In the mass spectrum at the bottom, the excitation (wave) phase switching according to principles of this invention was applied additionally to the aforementioned measures and results in the almost complete elimination of the 1v-subharmonic signals.

It should be mentioned here that the method is not restricted to 2ω-detection. In a second aspect, it is possible to apply it to multi electrode nω-detection with n>2. Applying the principles disclosed herein will reduce the (n−1, n−3, n−5, . . . )v-subharmonics and (n+1, n+3, n+5, . . . )v-harmonics. But with nω-detection, the very high abundant signals of the (n−2, n−4, n−6, . . . )v-subharmonics and harmonics are still apparent. Also the low abundance signals of (n+2, n+4, n+6, . . . )v-harmonics remain.

Figure 12:
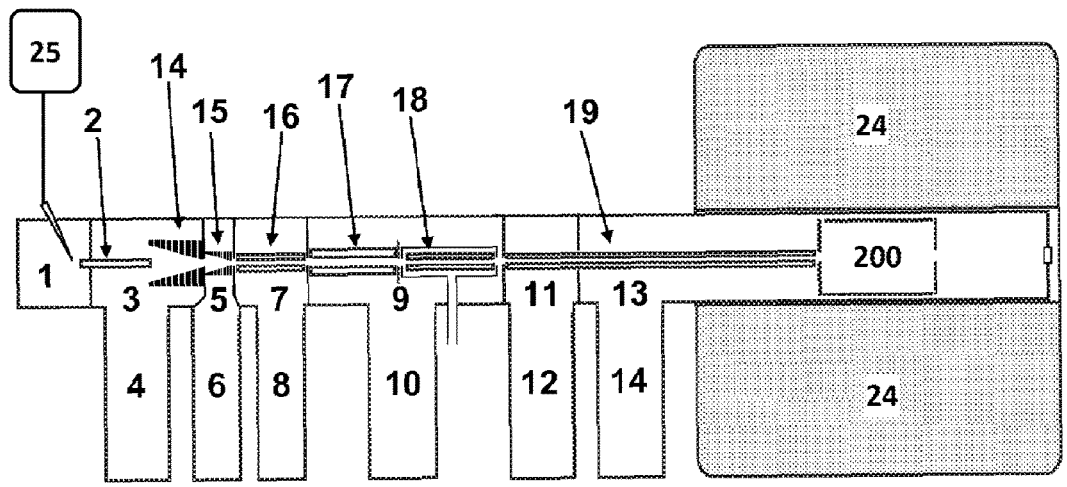
FIG. 12 shows by way of example an ICR-MS set-up suitable for carrying out the methods according to the invention.

The general operation and function of an ion cyclotron resonance mass spectrometer can be briefly described by way of example with reference to FIG. 12. Ions are produced preferably at substantially constant output, for example, by electrospray in a vacuum-external ion source (1). The ion source (1) might receive the liquid to be sprayed from an upstream substance separator (25), such as a liquid chromatograph or an electrophoretic device. The ions can be introduced, together with ambient gas, through a capillary (2) into the first stage (3) of a differential pumping system, which may consist of a series of chambers (3), (5), (7), (9), (11) and (13) and could be pumped by the pumps (4), (6), (8), (10), (12) and (14). Ions in the chambers (3) and (5) can be drawn in by the ion funnels (14) and (15) and transferred into the multipole ion guiding system (16), in which ions can be either guided through or also be stored. Storing allows in particular the repeated gated release of ion bunches having substantially the same ion count. The ions may be subsequently transferred through a quadrupole mass filter (17) and through another multipole ion guide (18) that also allows ion storage, and finally via the main ion transfer system (19) into the ICR cell (200), where they can be captured, trapped and detected.

The ICR cell (200) may consist of four mantle-shaped enclosing longitudinal electrodes (210) to (212) and of two axial trapping electrodes (205) and (206) with a central hole (20) in each of them, as has been set out with reference to FIG. 1. The ICR cell is preferably located in the homogeneous zone of a strong magnetic field that may be generated by superconducting coils in a helium cryostat (24) and should be kept as constant in time as well as spatially homogeneous as possible. The magnetic field is preferably aligned parallel to the longitudinal mantle electrodes of the ICR cell, as shown.

Figure 13:
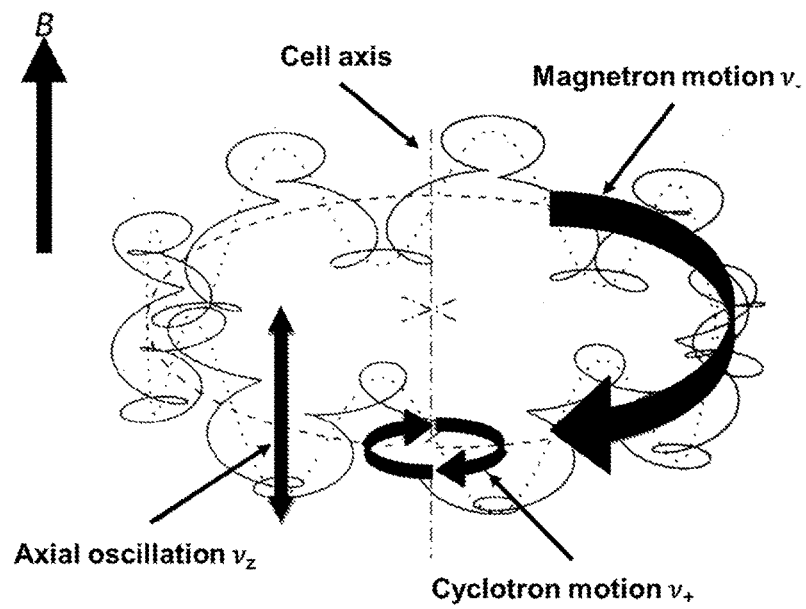
FIG. 13 shows the three independent ion motions of an ion in an ICR cell. Only the radial motions, the cyclotron motion with frequency $v_+$ and the magnetron motion with frequency $v_-$ are relevant for carrying out the methods according to principles of the invention. It should be mentioned that the orbit diameters of the radial motions are outlined schematically here in such a way as to give the impression that the cyclotron motion is a fast motion (small orbit) and the magnetron motion is a slow (drift) motion (large orbit). In fact, the cyclotron frequency is usually faster by a factor of approximately $10^5$, but the cyclotron orbit is usually larger than the magnetron orbit, contrary to what is shown.

The radial motions of an ion in an ICR cell which are relevant for carrying out the methods according to principles of the invention are the cyclotron motion with frequency $v_+$ and the magnetron motion with frequency $v_-$ with reference to FIG. 13. The cyclotron motion is a fast motion perpendicular to the magnetic field lines and the magnetron motion is a slow (drift) motion around the electric trapping field axis, the cyclotron frequency being typically higher by a factor of about $10^5$.

The invention has been described with reference to a number of different embodiments thereof. It will be understood, however, that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations as the case may be.

The invention claimed is:

1. A method for reducing 1ν-subharmonic signals in measurements of ICR mass spectra by quadrupolar 2ω-detection of transients representing ionic image currents in an ICR cell after excitation of ions, the method comprising the steps:
   exciting a first bunch of ions using a first excitation wave phase and measuring a first transient by 2ω-detection,
   exciting a second bunch of ions using a second excitation wave phase differing from the first phase by substantially 180°, and measuring a second transient by 2ω-detection,
   adding the first and second transients, and
   transforming a sum of the first and second transients into a frequency spectrum.

2. The method according to claim 1, being applied to a broad band measurement spanning an m/z range of equal to or more than 1000 Dalton.

3. The method according to claim 2, wherein the first and second bunches of ions are derived from a complex substance mixture.

4. The method according to claim 3, wherein the complex substance mixture is derived from one of crude oil, oil distillation residue, and a plant extract.

5. The method according to claim 1, wherein the first and the second bunches of ions comprise substantially equal numbers of ions.

6. The method according to claim 5, wherein the ions of the first and second bunches of ions are generated in an ion source which operates at substantially constant ionic output, and are transferred to the ICR cell using a same transfer procedure.

7. The method according to claim 6, wherein the ion source is fed with substances from a substance separator.

8. The method according to claim 7, wherein the substance separator is one of a chromatograph and an electrophoretic device.

9. The method according to claim 7, wherein the first and second transients are measured immediately subsequently.

10. The method according to claim 1, wherein a first sum-transient is obtained by adding measured transients from several bunches of ions using the first excitation wave phase, and a second sum-transient is obtained in a similar way but using the second excitation wave phase, and the first and second sum-transients are added to obtain the frequency spectrum by Fourier transformation.

11. The method according to claim 10, wherein the first and second sum-transients are obtained by alternately measuring and adding transients from several bunches of ions.

12. The method according to claim 1, wherein also a phase of detection is switched by 180° between a measurement of the first and second transients, and 1ν signals found therein are used to precisely determine an unperturbed cyclotron frequency $\nu_c$.

13. The method according to claim 1, wherein the frequency spectrum is transformed into a mass spectrum.

14. The method according to claim 1, wherein the excitation is dipolar.

15. The method according to claim 1, wherein the ICR cell comprises four quarter cylindrical mantle electrodes and two axial trapping electrodes.

16. The method according to claim 1, wherein the excitation includes irradiating the ICR cell with a pulse radio frequency sweep ("chirp").

17. A method for measuring ion cyclotron resonance transients that represent ionic image currents in an ICR cell, having 2×n mantle electrodes where n>2 is an integer, after excitation of ions, the method comprising the steps:
   exciting a first bunch of ions using a first excitation wave phase and measuring a first transient by nω-detection,
   exciting a second bunch of ions using a second excitation wave phase differing from the first phase by substantially 180°, and measuring a second transient by nω-detection, and
   adding the first and second transients to form a sum transient.

18. The method according to claim 17, wherein the sum transient is transformed into a frequency or mass spectrum.

19. The method according to claim 18, wherein an intensity of a group of (n−1)ν, (n−3)ν, (n−5)ν, ... subharmonic signals as well as a group of (n+1)ν, (n+3)ν, (n+5)ν, ... higher frequency harmonic signals is reduced as compared to that of a main peak $n\nu_+$ in the frequency or mass spectrum.

20. The method according to claim 17, wherein both an excitation wave phase as well as a detection phase is switched by substantially 180° between a measurement of the first and second transients.

* * * * *